(12) United States Patent
Hahn et al.

(10) Patent No.: US 10,519,199 B2
(45) Date of Patent: Dec. 31, 2019

(54) **VACCINE COMPOSITION COMPRISING RECOMBINANT PROTEIN FOR PREVENTING SWINE *MYCOPLASMA* INFECTION**

(71) Applicant: INNOVAC, Gangwon-do (KR)

(72) Inventors: Tae Wook Hahn, Seoul (KR); Kashinath Abhijit Barate, Gangwon-Do (KR); Ki Ju Kim, Gangwon-Do (KR); Woo Sung Shin, Gangwon-Do (KR)

(73) Assignee: INNOVAC, Gangwon-do (KR)

( * ) Notice: Subject to any disclaimer, the term of this patent is extended or adjusted under 35 U.S.C. 154(b) by 0 days.

(21) Appl. No.: 16/324,827

(22) PCT Filed: Aug. 14, 2017

(86) PCT No.: PCT/KR2017/008851
§ 371 (c)(1),
(2) Date: Feb. 11, 2019

(87) PCT Pub. No.: WO2018/030878
PCT Pub. Date: Feb. 15, 2018

(65) Prior Publication Data
US 2019/0177375 A1  Jun. 13, 2019

(30) Foreign Application Priority Data

Aug. 12, 2016 (KR) .................. 10-2016-0103259

(51) Int. Cl.
*A61K 39/02* (2006.01)
*C07K 14/30* (2006.01)
*A61K 39/00* (2006.01)

(52) U.S. Cl.
CPC .......... *C07K 14/30* (2013.01); *A61K 39/0241* (2013.01); *A61K 2039/552* (2013.01)

(58) Field of Classification Search
CPC ...................................... C07K 14/30
See application file for complete search history.

(56) References Cited

U.S. PATENT DOCUMENTS 9,028,828 B2 * 5/2015 Archambault ......... C07K 14/30
424/168.1

* cited by examiner

*Primary Examiner* — Albert M Navarro
(74) *Attorney, Agent, or Firm* — Marshall, Gerstein & Borun LLP

(57) ABSTRACT

Provided are a recombinant protein for producing a swine *Mycoplasma* infection-preventing vaccine composition, and a swine *Mycoplasma hyopneumoniae* and *Mycoplasma hyorhinis* infection-preventing vaccine composition including the recombinant protein. When the recombinant proteins for the vaccine production in accordance with the present disclosure are added to the swine *Mycoplasma* infection-preventing vaccine composition, the immune response to the swine *Mycoplasma hyopneumoniae* and swine *Mycoplasma hyorhinis* strain and the immune response to the P97 protein are increased. As a result, the present vaccine exhibits a defensive effect superior to an existing commercially available vaccine. Therefore, the recombinant proteins for the vaccine production according to the present disclosure and the vaccine compositions using the recombinant proteins may effectively prevent diseases caused by the *Mycoplasma hyopneumoniae* and *Mycoplasma hyorhinis* infection, especially, swine *Mycoplasma*-derived pneumonia and swine *Mycoplasma*-derived arthritis.

20 Claims, 7 Drawing Sheets

Specification includes a Sequence Listing.

[FIG. 1]
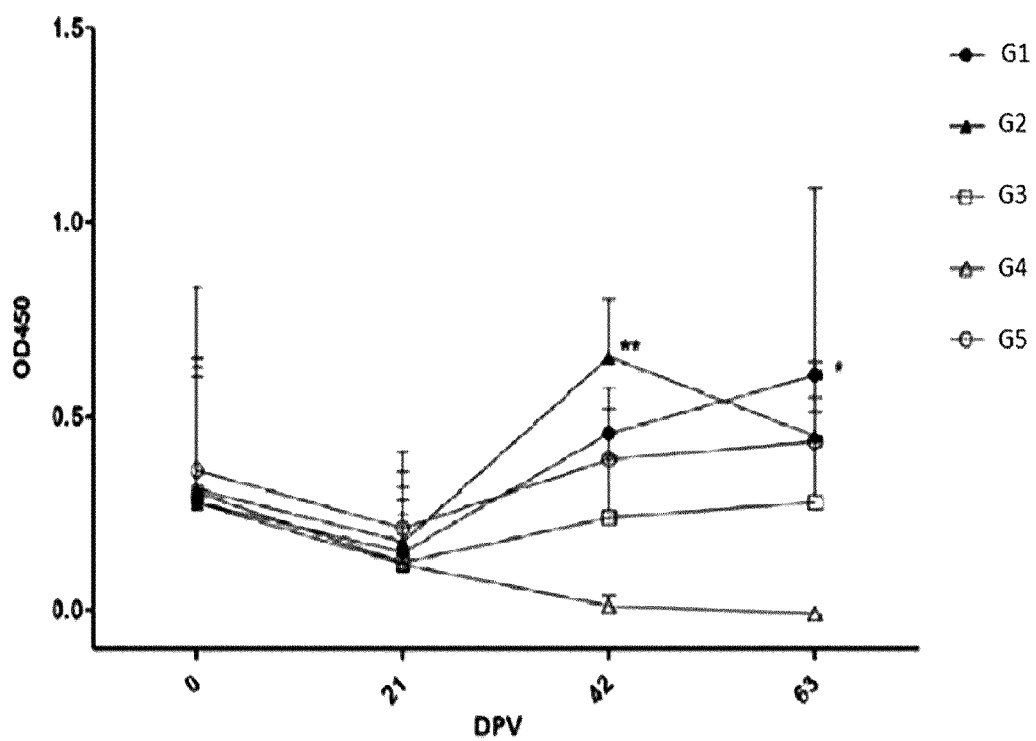

【FIG. 2】
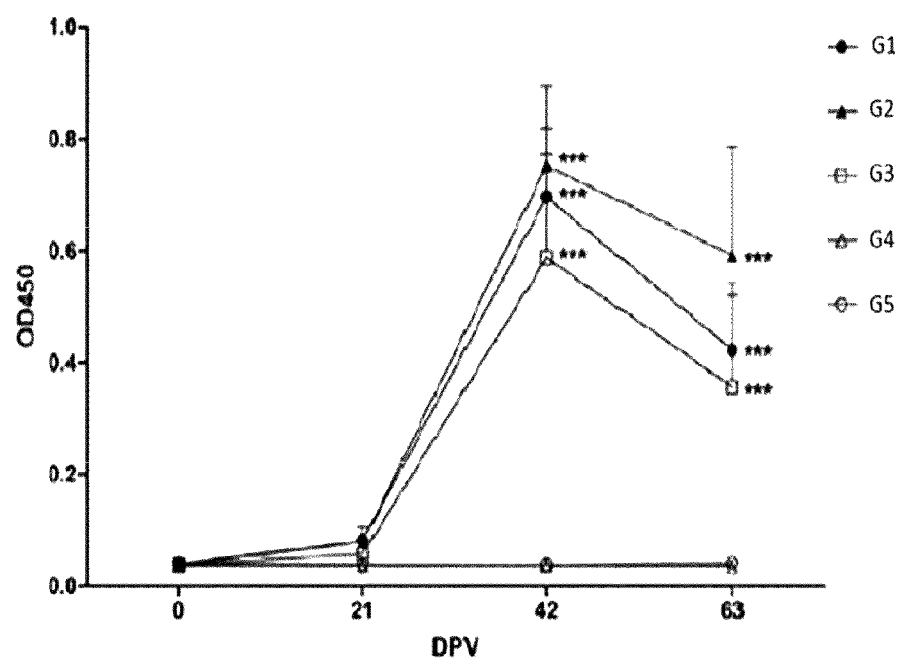
【FIG. 3A】

[FIG. 3B]

[FIG. 4]
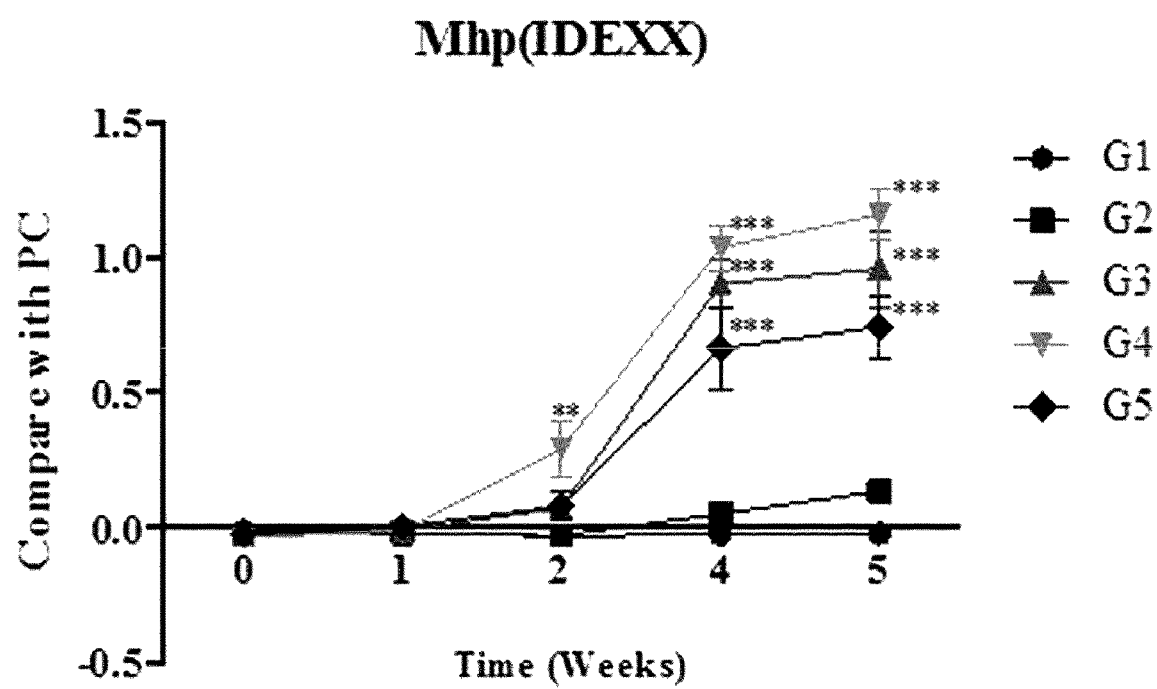

[FIG. 5]
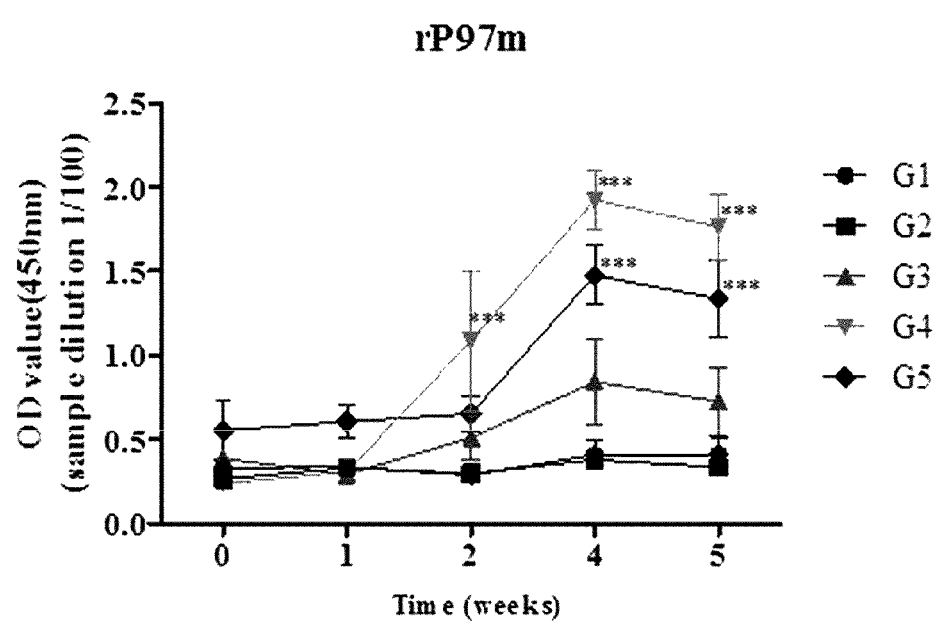

[FIG. 6]
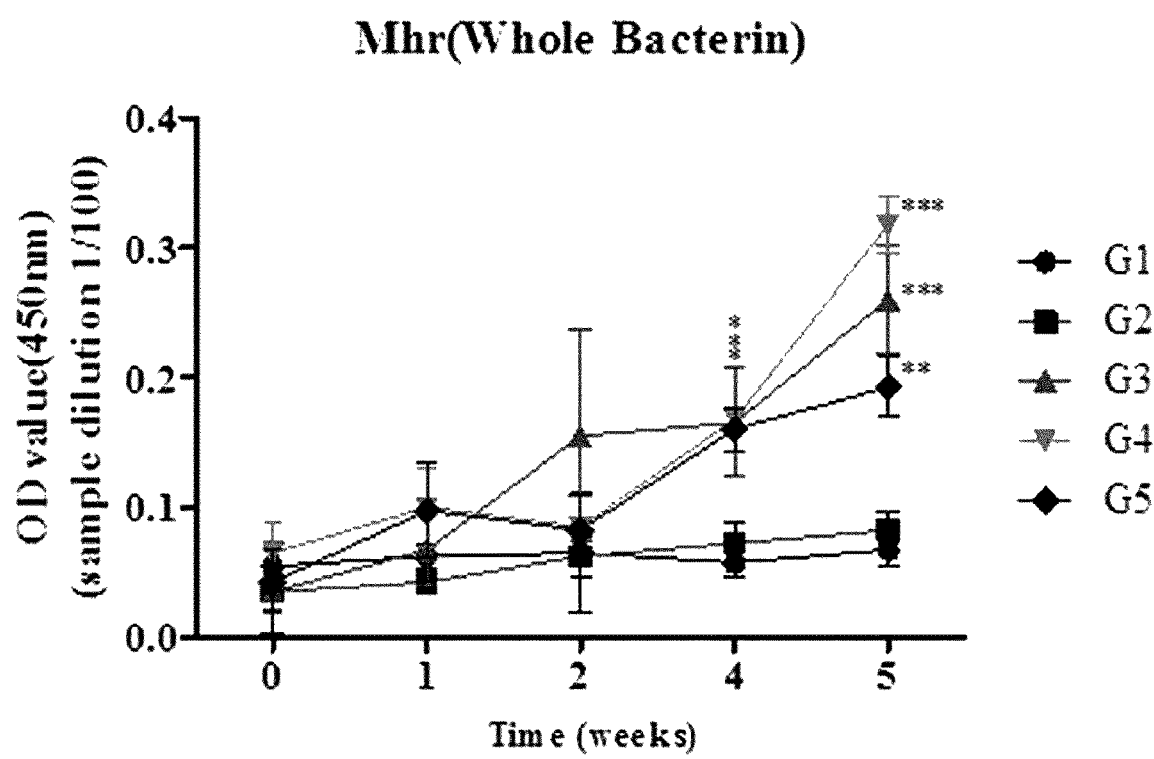

【FIG. 7】
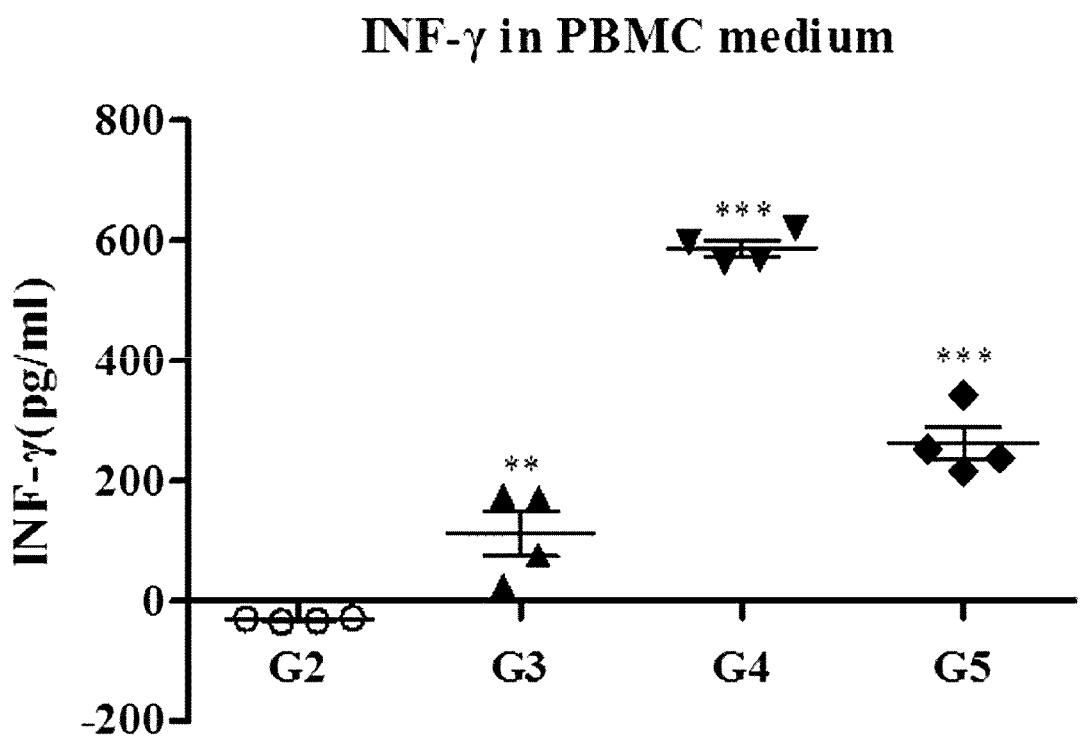
【FIG. 8】
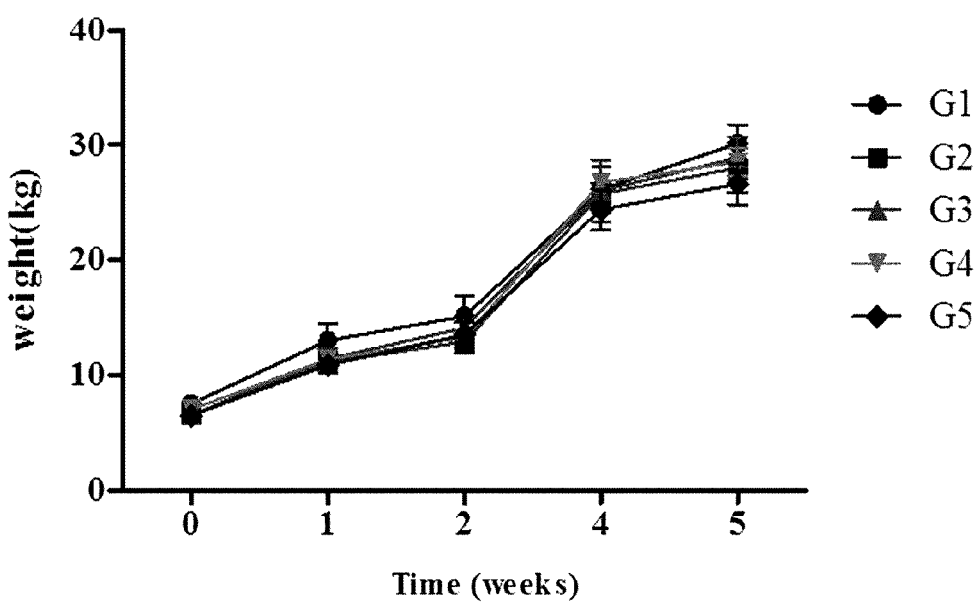

VACCINE COMPOSITION COMPRISING RECOMBINANT PROTEIN FOR PREVENTING SWINE *MYCOPLASMA* INFECTION

TECHNICAL FIELD

The present disclosure relates to a recombinant protein for producing a swine *Mycoplasma* infection-preventing vaccine composition, and to a swine *Mycoplasma hyopneumoniae* and *Mycoplasma hyorhinis* infection-preventing vaccine composition including the recombinant protein.

BACKGROUND ART

*Mycoplasma hyopneumoniae* is a respiratory pathogen associated with porcine respiratory disease complex (PRDC) and enzootic pneumonia (EP). *Mycoplasma hyopneumoniae* may have colonization on respiratory cilium cells to cause infection thereof to act as a cause of the swine *mycoplasma* pneumonia.

*Mycoplasma hyopneumoniae* single infection causes symptoms such as dry cough. However, when *Mycoplasma hyopneumoniae* is combined infection with other respiratory pathogens, this causes serious respiratory symptoms, decreases the activity of macrophages, and also causes losing a primary defense function that prevents intrusion of other pathogens, thereby to increase the risk of additional pathogen infection.

In addition to *Mycoplasma hyopneumoniae, Mycoplasma hyorhinis* has emerged as a new pathogen for swine respiratory infections. *Mycoplasma hyorhinis* has been reported to be mixed infection with swine genital respiratory virus to exacerbate the pathology. *Mycoplasma hyorhinis* alone is also known to cause *mycoplasma* (hepatic) lesions expressed in *Mycoplasma hyopneumoniae*. In addition, *Mycoplasma hyorhinis* also produce same hepatic lesions in lung as *Mycoplasma hyopneumoniae* dose and is a highly pathogenic pathogen.

To prevent *Mycoplasma hyopneumoniae* infection which causes great damage to swine farms, inactivated vaccine has currently been commercialized and used. This inactivated vaccine is currently only a vaccine available for the swine *Mycoplasma* pneumonia. However, most of the commercially available *Mycoplasma hyopneumoniae* inactivated vaccines fail to form antibodies after inoculation to the swine. Although clinical symptoms may be alleviated by the commercially available *Mycoplasma hyopneumoniae* inactivated vaccines, the commercially available *Mycoplasma hyopneumoniae* inactivated vaccines have a technical limitation in that the commercially available *Mycoplasma hyopneumoniae* inactivated vaccines cannot prevent natural infection and colonization of the *Mycoplasma hyopneumoniae* on respiratory cilium cells. Therefore, it is important to develop an effective vaccine to solve these problems.

The *Mycoplasma hyopneumoniae* infection is initiated when pathogens attach to the ciliates of respiratory epithelial cells. Adhesin P97 is a membrane surface protein of *Mycoplasma hyopneumoniae* and is known to be a highly immunogenic antigen. At a C-terminus of the P97, there are R1 and R2 sites which are repeated. The R1 site binds to an attachment site (AAKPV/E) of the host respiratory cilia. The bound *Mycoplasma hyopneumoniae* may obtain amino acid required for growth from the host. The *Mycoplasma hyopneumoniae* may cause the molecules of the host to be arranged in various ways in order to invade an injured tissue. On the other hand, the host may produce antibodies that prevent the attachment of the *Mycoplasma hyopneumoniae* to the swine cilium or may inhibit the growth of attached pathogens. However, previous studies have reported that conventional commercial vaccines cannot induce antibodies to P97.

Therefore, there is a need for a novel vaccine that can prevent natural infections of swine *mycoplasma* infection, especially *Mycoplasma hyopneumoniae* and *Mycoplasma hyorhinis*, and effectively form antibodies.

DISCLOSURE

Technical Problem

While the present inventors were developing a vaccine to effectively prevent *Mycoplasma hyopneumoniae* and *Mycoplasma hyorhinis*, the present inventors have confirmed that a vaccine including a recombinant P97 protein using *Mycoplasma hyopneumoniae*-derived adhesion protein P97 protein exhibits a significantly superior immune response to conventional commercial vaccines. In this way, the present disclosure has been achieved.

Therefore, a purpose of the present disclosure is to provide a recombinant protein for production of a vaccine for prevention of swine *Mycoplasma hyopneumoniae* infection, where the protein is composed of an amino acid sequence represented by SEQ ID NO.: 1. Further, a purpose of the present disclosure is to also provide a *Mycoplasma hyopneumoniae* infection-preventing vaccine composition including the recombinant protein.

Another purpose of the present disclosure is to provide a recombinant protein for production of a vaccine for prevention of swine *Mycoplasma hyopneumoniae* and *Mycoplasma hyorhinis* infection, in which the protein is composed of an amino acid sequence represented by SEQ ID NO.: 13. Further, a purpose of the present disclosure is to also provide a *Mycoplasma hyopneumoniae* and *Mycoplasma hyorhinis* infection-preventing vaccine composition including the recombinant protein.

Technical Solution

In order to achieve the above purposes, the present disclosure provides a recombinant protein for production of a vaccine for prevention of swine *Mycoplasma hyopneumoniae* infection, the protein including an amino acid sequence represented by SEQ ID NO.: 1.

Further, the present disclosure provides polynucleotides encoding the recombinant protein.

Further, the present disclosure provides a vaccine composition for preventing *Mycoplasma hyopneumoniae* infection, in which the composition includes the recombinant protein.

Further, the present disclosure provides a *Mycoplasma hyopneumoniae* infection-preventing vaccine adjuvant including the recombinant protein.

Further, the present disclosure provides a vaccine composition for preventing a disease caused by *Mycoplasma hyopneumoniae* infection, the composition including the recombinant protein.

Further, the present disclosure provides a method for producing *Mycoplasma hyopneumoniae* infection-preventing vaccine adjuvants, in which the method includes 1) producing a vector including a polynucleotide encoding a recombinant protein represented by SEQ ID NO.: 1; 2) transforming a host using the vector; and 3) expressing the recombinant protein in the transformed host.

Further, the present disclosure provides a method for preventing swine *Mycoplasma hyopneumoniae* infection, in which the method includes inoculating the vaccine composition to a swine.

Further, the present disclosure provides a recombinant protein for production of a vaccine for swine *Mycoplasma hyopneumoniae* and *Mycoplasma hyorhinis* infection-prevention, in which the protein comprises an amino acid sequence represented by SEQ ID NO.: 13.

Further, the present disclosure provides a polynucleotide encoding the recombinant protein.

Further, the present disclosure provides a swine *Mycoplasma hyopneumoniae* and *Mycoplasma hyorhinis* infection-preventing vaccine composition including the recombinant protein.

Further, the present disclosure provides a swine *Mycoplasma hyopneumoniae* and *Mycoplasma hyorhinis* infection-preventing vaccine adjuvant including the recombinant protein.

Further, the present disclosure provides a vaccine composition for preventing a disease caused by swine *Mycoplasma hyopneumoniae* and *Mycoplasma hyorhinis* infection, in which the composition includes the recombinant protein.

Further, the present disclosure provides a method for producing a swine *Mycoplasma hyopneumoniae* and *Mycoplasma hyorhinis* infection-preventing vaccine adjuvant, the method including 1) producing a vector including a polynucleotide encoding a recombinant protein represented by SEQ ID NO.: 13; 2) transforming a host using the vector; and 3) expressing the recombinant protein in the transformed host.

Further, the present disclosure provides a method for preventing swine *Mycoplasma hyopneumoniae* and *Mycoplasma hyorhinis* infection, the method including inoculating the vaccine composition to a swine.

Advantageous Effects

When the recombinant proteins for the vaccine production in accordance with the present disclosure are added to the swine *Mycoplasma* infection-preventing vaccine composition, the immune response to the swine *Mycoplasma hyopneumoniae* and swine *Mycoplasma hyorhinis* strain and the immune response to the P97 protein are increased. As a result, the present vaccine exhibits a defensive effect superior to an existing commercially available vaccine. Therefore, the recombinant proteins for the vaccine production and the vaccine compositions using the recombinant proteins may effectively prevent diseases caused by the *Mycoplasma hyopneumoniae* and *Mycoplasma hyorhinis* infection, especially, swine *Mycoplasma*-derived pneumonia and swine *Mycoplasma*-derived arthritis.

DESCRIPTION OF DRAWINGS

FIG. 1 illustrates results of identification of *Mycoplasma hyopneumoniae*-specific antibodies after swine *Mycoplasma* one-valent vaccine including rP97 protein was inoculated to a 3-week-old swine. All experimental data are expressed as mean±S.D. Significant differences between the vaccine and PBS groups were expressed as * (P<0.05) and ** (P<0.01) (G1: Mhp HID3138+rP97 recombinant protein-containing lysate, G2: Mhp HID3117+rP97 recombinant protein-containing lysate, G3: rP97 recombinant protein-containing lysate, G4: saline alone, G5: commercialized vaccine Mycoflex®) (DPV: Days post vaccination).

FIG. 2 illustrates results of evaluating rP97-specific antibody titers using an indirect ELISA after inoculation of a swine *Mycoplasma* one-valent vaccine including rP97 protein into a 3-week-old swine. All experimental data are expressed as mean±S.D. Significant differences between the vaccine and PBS groups were expressed as *** (P<0.001) (G1: Mhp HID3138+rP97 recombinant protein-containing lysate, G2: Mhp HID3117+rP97 recombinant protein-containing lysate, G3: rP97 recombinant protein-containing lysate, G4: saline alone, G5: commercialized vaccine Mycoflex®) (DPV: Days post vaccination).

FIG. 3A illustrates a comparison between modeling structures of rP97m recombinant protein represented by SEQ ID NO.: 1 and rP97m recombinant protein represented by SEQ ID NO.: 13.

FIG. 3B illustrates a comparison between rP97m recombinant protein represented by SEQ ID NO.: 1 and rP97m recombinant protein represented by SEQ ID NO.: 13.

FIG. 4 illustrates results of *Mycoplasma hyopneumoniae*-specific antibody using IDEXX *M. hyo* ELISA with serums obtained from a swine before the swine *Mycoplasma* two-valent vaccine including rP97m recombinant protein was inoculated thereto, and up to 5 weeks after the inoculation thereof. All experimental data are expressed as mean±S.D. Significant differences between the vaccine and PBS groups were expressed as  (P<0.01) and * (P<0.001) (G1: PBS alone, G2: commercialized vaccine Respisure®, G3: Mhp HID3134+Mhr HID3224+rP97m, G4: Mhp HID3140+Mhr HID3224+rP97m, G5: Mhp HID3138+Mhr HID3224+rP97m).

FIG. 5 illustrates results of evaluating rP97m-specific antibody titers using an indirect ELISA with serums obtained from a swine before the swine *Mycoplasma* two-valent vaccine including rP97m recombinant protein was inoculated thereto, and up to 5 weeks after the inoculation thereof. All experimental data are expressed as mean±S.D. Significant differences between the vaccine and PBS groups were expressed as *** (P<0.001) (G1: PBS alone, G2: commercialized vaccine Respisure®, G3: Mhp HID3134+Mhr HID3224+rP97m, G4: Mhp HID3140+Mhr HID3224+rP97m, G5: Mhp HID3138+Mhr HID3224+rP97m).

FIG. 6 illustrates results of evaluating *Mycoplasma hyorhinis*-specific antibody titers using an indirect ELISA test with serums obtained from a swine before the swine *Mycoplasma* two-valent vaccine including rP97m recombinant protein was inoculated thereto, and up to 5 weeks after the inoculation thereof, where in the ELISA test, all of *Mycoplasma hyorhinis* was used as antigens. All experimental data are expressed as mean±S.D. Significant differences between the vaccine and PBS groups were expressed as ** (P<0.01) (G1: PBS alone, G2: commercialized vaccine Respisure®, G3: Mhp HID3134+Mhr HID3224+rP97m, G4: Mhp HID3140+Mhr HID3224+rP97m, G5: Mhp HID3138+Mhr HID3224+rP97m).

FIG. 7 illustrates results of evaluating interferon gamma productions after PBMC (Peripheral Blood Mononuclear Cell) was isolated from blood obtained at 2 weeks after inoculation of a swine with a swine *Mycoplasma* two-valent vaccine including rP97m recombinant protein, and, then, the PBMC were stimulated with *Mycoplasma hyopneumoniae* inactivated strain. All experimental data are expressed as mean±S.D. Significant differences between the vaccine group and the commercial vaccine group were  (P<0.05) and * (P<0.001) (G1: PBS alone, G2: commercially available vaccine Respisure®, G3: Mhp HID3134+Mhr HID3224+rP97m, G4: Mhp HID3140+Mhr HID3224+rP97m, G5: Mhp HID3138+Mhr HID3224+rP97m).

FIG. 8 illustrates results of comparing swine weight changes before and after the inoculation of the swine with the swine *Mycoplasma* two-valent vaccine including rP97m recombinant protein (G1: PBS alone, G2: commercially available vaccine Respisure®, G3: Mhp HID3134+Mhr HID3224+rP97m, G4: Mhp HID3140+Mhr HID3224+rP97m, G5: Mhp HID3138+Mhr HID3224+rP97m).

BEST MODES OF THE INVENTION

The present disclosure provides a recombinant protein for production of a vaccine for swine *Mycoplasma hyopneumoniae* infection prevention, the protein being consist of an amino acid sequence represented by SEQ ID NO.: 1, and provides a polynucleotide encoding the recombinant protein.

Further, the present disclosure provides a recombinant protein for production of a vaccine for swine *Mycoplasma hyopneumoniae* and *Mycoplasma hyorhinis* infection prevention, the protein being consist of an amino acid sequence represented by SEQ ID NO.: 13 and provides a polynucleotide encoding the recombinant protein.

Further, the present disclosure provides a use of a recombinant protein for production of a vaccine for swine *Mycoplasma hyopneumoniae* infection prevention, the protein being consist of an amino acid sequence represented by SEQ ID NO.: 1.

Further, the present disclosure provides a use of a recombinant protein for production of a vaccine for swine *Mycoplasma hyopneumoniae* and *Mycoplasma hyorhinis* infection prevention, the protein being consist of an amino acid sequence represented by SEQ ID NO.: 13.

Further, the present disclosure provides a recombinant protein for use in the production of a vaccine for swine *Mycoplasma hyopneumoniae* infection prevention, the protein being consist of an amino acid sequence represented by SEQ ID NO.: 1.

Further, the present disclosure provides a recombinant protein for use in the production of a vaccine for swine *Mycoplasma hyopneumoniae* and *Mycoplasma hyorhinis* infection prevention, the protein being consist of an amino acid sequence represented by SEQ ID NO.: 13.

When the recombinant protein consisted of the amino acid sequence represented by the SEQ ID NO.: 1 is included in a one-valent vaccine for *Mycoplasma hyopneumoniae* infection prevention, P97, which is involved in early infection and adherence of the *Mycoplasma hyopneumoniae*, can more effectively induce cellular and humoral immune responses against *Mycoplasma hyopneumoniae* and thus induce more effective immune responses compared to commercial vaccines. In the present specification, this recombinant protein is referred to as 'rP97'.

When the recombinant protein consisted of the amino acid sequence represented by the SEQ ID NO.: 13 is included in a two-valent vaccine for *Mycoplasma hyopneumoniae* and *Mycoplasma hyorhinis* infection prevention, P97, which is involved in early infection and adherence of the *Mycoplasma hyopneumoniae* and *Mycoplasma hyorhinis*, can more effectively induce cellular and humoral immune responses against *Mycoplasma hyopneumoniae* and *Mycoplasma hyorhinis* and thus induce more effective immune responses compared to commercial vaccines. In the present specification, this recombinant protein is referred to as 'rP97m'.

The recombinant proteins rP97 and rP97m may be produced by fusing *Mycoplasma hyopneumoniae*-derived P97 protein and the *E. coli* heat-labile enterotoxin subunit B gene (eltb). More specifically, the recombinant proteins rP97 and rP97m may be produced by fusing the C-terminal repeating sequences R1 and R1R2 of *Mycoplasma hyopneumoniae* P97 gene and the *E. coli* gene (eltb) and, then, amplifying ltbR1 and ltbR1R2 as P97 genes fused with LTB via polymerase chain reaction (PCR).

The recombinant protein of the present disclosure may include all of polypeptides having at least 70%, 80%, 90%, 95%, 98% or preferably at least 99% homology with an amino acid sequence represented by SEQ ID NO.: 1 or SEQ ID NO.: 13. As used herein, "homology" refers to a measure of the similarity between protein or polynucleotide sequences. These polypeptides may have deletion, addition or substitution of at least one amino acid compared to the amino acid sequence represented by the SEQ ID NO.: 1 or SEQ ID NO.: 13. A score of the homology between two sequences is based on a percentage of identities and/or preservation of substitutions of the sequence.

When the recombinant proteins in accordance with the present disclosure are used to produce vaccines, the recombinant proteins may be added to the vaccine in purified protein form or may be expressed in *E. coli* and be included in the vaccine in a lysate state in a non-purified form. When the recombinant protein is included in the lysate state, the concentration of the lysate may be in a range of 0.2 to 0.3 mg/ml.

Further, the present disclosure provides polynucleotides encoding the recombinant proteins. The polynucleotide may include all possible sequences encoding the amino acid sequence represented by the SEQ ID NO.: 1 or 13, respectively. Preferably, the polynucleotide may be consisted of a base sequence represented by SEQ ID NO.: 2 or SEQ ID NO.: 14. The polynucleotide may have at least 70%, 80%, 90%, 95%, 98% or preferably at least 99% homology with a base sequence represented by the SEQ ID NO.: 2 or SEQ ID NO.: 14. Alternatively, the polynucleotide may include all polynucleotides capable of maintaining the biological activity of the SEQ ID NO.: 2 or SEQ ID NO.: 14.

Further, the present disclosure provides a *Mycoplasma hyopneumoniae* (*M. hyopneumoniae*) infection-preventing vaccine composition including the recombinant protein rP97.

The *Mycoplasma hyopneumoniae* infection-preventing vaccine composition in accordance with the present disclosure may refer to a one-valent vaccine composition that can prevent the *Mycoplasma hyopneumoniae* infection in the swine and prevent early infection thereof. The recombinant protein used for producing the vaccine for swine *Mycoplasma hyopneumoniae* infection prevention and consisted of the amino acid sequence represented by the SEQ ID NO.: 1 in accordance with the present disclosure may be included in the vaccine composition to form a P97-specific antibody to further promote the immune response induced by the inactivated *Mycoplasma hyopneumoniae* included in the vaccine.

Further, the present disclosure provides a *Mycoplasma hyopneumoniae* and *Mycoplasma hyorhinis* infection-preventing vaccine composition including the recombinant protein rP97m.

The *Mycoplasma hyopneumoniae* and *Mycoplasma hyorhinis* infection-preventing vaccine composition in accordance with the present disclosure may refer to a two-valent vaccine composition that can prevent the *Mycoplasma hyopneumoniae* and *Mycoplasma hyorhinis* infection in the swine and prevent early infection thereof. The recombinant protein used for producing the vaccine for swine *Mycoplasma hyopneumoniae* and *Mycoplasma hyorhinis* infection prevention and consisted of the amino acid sequence represented by the SEQ ID NO.: 13 in accordance with the present disclosure may be included in the vaccine composition to form a P97-specific antibody to further promote the immune response induced by the inactivated *Mycoplasma hyopneumoniae* and *Mycoplasma hyorhinis* included in the vaccine.

Therefore, the vaccine composition in accordance with the present disclosure may further include the inactivated *Mycoplasma hyopneumoniae* or *Mycoplasma hyorhinis*.

As used herein, the term "inactivated" means "*mycoplasma*-killed". Such inactivated *mycoplasma* may be purchased or produced from live cells in a manner well known in the art.

The inactivated *mycoplasma*, which is included in the vaccine composition according to the present disclosure, may include both a standard strain whose immunity inducing effect may be enhanced by the recombinant protein according to the present disclosure or a highly pathogenic and high-titer stain which forms an antibody, wherein the highly pathogenic and high-titer strain isolated from the *mycoplasma*-infected swine. Alternatively, preferably, the inactivated *mycoplasma* may be a *mycoplasma* that may effectively induce an antibody to the whole *mycoplasma* and the P97 critical antigen upon inoculation together with the recombinant protein according to the present disclosure.

The *Mycoplasma hyopneumoniae* or *Mycoplasma hyorhinis* in the vaccine composition may be included in the vaccine at a concentration of $1.0 \times 10^6$ to $1.0 \times 10^{10}$ CCUs (colour-changing units)/ml. Preferably, the *Mycoplasma hyopneumoniae* or *Mycoplasma hyorhinis* in the vaccine composition may be included in the vaccine at a concentration of $1.0 \times 10^7$ to $1.0 \times 10^{10}$ CCUs (colour-changing units)/ml. More preferably, the *Mycoplasma hyopneumoniae* or *Mycoplasma hyorhinis* in the vaccine composition may be included in the vaccine at a concentration of $1.0 \times 10^8$ to $1.0 \times 10^{10}$ CCUs (colour-changing units)/ml.

The vaccine composition according to the present disclosure may include an adjuvant mixture which may enhance the immunogenicity of the vaccine to induce protective immunity even with minimal administration, and may include one or more pharmaceutically or veterinarily acceptable carriers, excipients or diluents. The term "pharmaceutically or veterinarily acceptable" composition as used herein refers to compositions that are physiologically acceptable and do not normally cause an allergic or similar reaction such as a gastrointestinal disorder, or dizziness when administered to an animal. Examples of the carrier, excipient and diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, water, methylhydroxybenzoate, propylhydroxybenzoate, talc, magnesium stearate and mineral oil. Further, fillers, anticoagulants, lubricants, wetting agents, fragrances, emulsifiers and preservatives may also be added to the vaccine composition. Carriers suitable for use may include, but are not limited to, saline, phosphate buffered saline, a minimal essential medium (MEM), or an aqueous medium including MEM of HEPES buffer. The adjuvant mixture for use in the vaccine composition according to the present disclosure include an oil that enhance the immune response and is metabolizable.

Further, the vaccine composition according to the present disclosure may be formulated using methods known in the art so as to provide rapid, sustained or delayed release of the active ingredient after administration of the composition to the mammals. The formulations may be in the form of powders, granules, tablets, emulsions, syrups, aerosols, soft or hard gelatine capsules, sterile injectable solutions, sterile powders and the like. The vaccine composition according to the present disclosure may be administered through a muscle, subcutaneous, transdermal, intravenous, intranasal, intraperitoneal or oral route, preferably intramuscularly or subcutaneously. According to the present disclosure, in one embodiment, the vaccine may include inactivated *Mycoplasma hyopneumoniae* and *Mycoplasma hyorhinis*, metabolizable oil, polyoxyethylene-polyoxypropylene block copolymer and acrylic acid polymer in the form of an oil-in-water emulsion. The dose of the vaccine may be appropriately selected depending on various factors such as route of administration, age, sex, weight, and severity of the animal.

Further, the vaccine composition according to the present disclosure may be produced by standard methods in the art, except for a feature process in accordance with the present disclosure, such as the production of the rP97 or rP97m recombinant protein. For example, the organism may be grown in a culture medium such as a complete medium. The proliferation of the organism may be monitored by standard techniques such as measuring a color change unit (CCU). The organisms may be collected when a sufficiently high-titer is achieved. The stock may be further concentrated or lyophilized by conventional methods before being packaged in a vaccine for formulation.

Further, the present disclosure provides a *Mycoplasma hyopneumoniae* infection-preventing vaccine adjuvant including the recombinant protein rP97, or a *Mycoplasma hyopneumoniae* and *Mycoplasma hyorhinis* infection-preventing vaccine adjuvant including the recombinant protein rP97m.

The vaccine adjuvant may refer to a substance that promotes immunogenicity and enhances the efficacy of the inactivated vaccine. The vaccine adjuvant may be inoculated simultaneously or sequentially with the vaccine including the inactivated *Mycoplasma hyopneumoniae* and/or *Mycoplasma hyorhinis* to further amplify the immune response in the subject resulting from the inactivated *Mycoplasma hyopneumoniae* and/or *Mycoplasma hyorhinis*.

Further, the present disclosure provides a vaccine composition for preventing a disease caused by the *Mycoplasma hyopneumoniae* infection, the composition including the recombinant protein rP97, or provides a vaccine composition for preventing a disease caused by the *Mycoplasma hyopneumoniae* and *Mycoplasma hyorhinis* infection, the composition including the recombinant protein rP97m.

The disease caused by the *Mycoplasma hyopneumoniae* and/or *Mycoplasma hyorhinis* infection may include, without limitation, various clinical diseases caused by the infection of the pathogen to the subject. Preferably, the disease may include porcine respiratory complex syndrome (PRCS), porcine pandemic pneumonia or *Mycoplasma hyorhinis*-derived arthritis.

Further, the present disclosure provides a method for producing the *Mycoplasma hyopneumoniae* infection-preventing vaccine adjuvant. The method includes: 1) producing a vector including a polynucleotide encoding a recombinant protein represented by SEQ ID NO.: 1; 2) transforming a host with the vector; and 3) expressing the recombinant protein in the transformed host.

Further, the present disclosure provides a method for producing the swine *Mycoplasma hyopneumoniae* and *Mycoplasma hyorhinis* infection-preventing vaccine adjuvant. The method includes 1) producing a vector including a polynucleotide encoding a recombinant protein represented by SEQ ID NO.: 13; 2) transforming a host with the vector; and 3) expressing the recombinant protein in the transformed host.

Further, the present disclosure provides a method for preventing the swine *Mycoplasma hyopneumoniae* infection, the method including inoculating a swine with the swine *Mycoplasma hyopneumoniae* infection-preventing vaccine composition including the recombinant protein rP97.

Further, the present disclosure provides a *Mycoplasma hyopneumoniae* and *Mycoplasma hyorhinis* infection-prevention method including inoculating a swine with the swine *Mycoplasma hyopneumoniae* and *Mycoplasma hyorhinis* infection-preventing vaccine composition including the recombinant protein rP97m.

The swine may include unlimited types of swine which may be potentially infected with the *mycoplasma*. Such infection prevention methods may be used in parallel with other therapeutic or prevention methods known in the art. The term "inoculation" used herein means providing to a subject a composition in accordance with the present disclosure in any suitable manner.

Hereinafter, the present disclosure is illustrated in more detail with reference to the Example. It should be understood, however, that the present disclosure is not limited to the Example.

MODES OF THE INVENTION

Example 1. One-Valent Vaccine Including rP97 Protein

1.1 Preparation of *Mycoplasma hyopneumoniae* Inactivation Strain

*Mycoplasma hyopneumoniae* (*M. hypneumoniae*, Mhp) strain was isolated from swine of domestic pig farms. Then, a protein pattern analysis confirmed that Mhp HID3117 and HID3138, which are isolated from the strain are different from the standard strain, *Mycoplasma hyopneumoniae* (Mhp) J (ATCC 25934). *Mycoplasma hyopneumoniae* strains, HID3117 and HID3138, were cultured for 3 weeks at 5% $CO_2$ and 37° C. using Friis medium. The cultured inoculum was inactivated by increasing the pH up to about 7.8. Bacterial inactivation was carried out using an inactivating reagent such as Binary ethyleneimine (BEI) (U.S. Pat. No. 5,565,205). BEI was produced by adding 2-bromoethylaminehydrobromide (BEA) (Sigma Aldrich, St. Louis, Mo., USA) to the culture liquid. Thereafter, BEI was neutralized by adding thereto sodium thiosulfate (Sigma Mo., USA) to the culture liquid. Thereafter, BEI was neutralized by adding thereto sodium thiosulfate (Sigma , St. Louis, Mo., USA) as a neutralizing reagent. A portion of the inactivated culture liquid was added to a new medium and cultured at 37° C., and was cultured for at least one week. Then, the inactivated state of the inactivated culture liquid was checked. Then, the inactivated culture liquid was concentrated by filtration or centrifugation.

1.2 Production of Recombinant rP97 Protein

The recombinant rP97 protein was produced by fusing the P97 protein of *Mycoplasma hyopneumoniae* and the *E. coli* heat-labile enterotoxin subunit B gene (eltb). More specifically, for Mhp HID3138 and Mhp HID3117 strains as domestic isolate strains, genomic DNA thereof was extracted using the genomic DNA extraction mini kit (RBC Biosciences). The genomic DNA of *Escherichia coli* was extracted by boiling method. The *E. coli* heat-labile enterotoxin subunit B gene (eltb) was fused with the C-terminal repeating sequence (R1 and R1R2) of the P97 gene. ltbR1 and ltbR1R2 as P97 genes being fused with LTB, were amplified by polymerase chain reaction (PCR). The primers used in the PCR are as shown in Table 1 below.

TABLE 1

| Target | Primer pairs | Reaction condition | Product size |
|---|---|---|---|
| *Escherichia coli* heat-labile enterotoxin subunit B gene (eltb) | LTBF: 5'-CAC CAT GGC TCC CCA GAC TAT TAC A-3'<br>LTBR: 5'-CTG GAT CCC CAT ACT GAT TGC-3' | 95° C. 20s, 57.5° C. 40s, 72° C. 15s, 30cycles | 300 bp |
| P97 gene (r1) | R1F: 5'-CAC CAT GGG GAT CCC TAC AAA AGA AG-3'<br>R1R: 5'-GCC AAG CTT AGT AGC AAC TGG T-3' | 95° C. 20s, 56.5° C. 40s, 72° C. 15s, 30cycles | 280 bp |
| P97 gene (r1r2) | R1F: 5'-CAC CAT GGG GAT CCC TAC AAA AGA AG-3'<br>2RsR: 5'-GGT AGT TGG GCT TTG TTG-3' | 95° C. 20s, 49.5° C. 40s, 72° C. 30s, 30cycles | 697 bp |
| Ltbr1 | LTBF: 5'-CAC CAT GGC TCC CCA GAC TAT TAC A-3'<br>R1R: 5'-GCC AAG CTT AGT AGC AAC TGG T-3' | 95° C. 20s, 56.5° C. 40s, 72° C. 30s, 30cycles | 582 bp |
| Ltbr1r2 | LTBF: 5'-CAC CAT GGC TCC CCA GAC TAT TAC A-3'<br>2RsR: 5'-GGT AGT TGG GCT TTG TTG-3' | 95° C. 20s, 49.5° C. 40s, 72° C. 40s, 30cycles | 1000 bp |

*Primer designed in this study. Other primer sequences were obtained from previous study (Conceicao et al., 2006).

The PCR products amplified using LTBF and R1F primers including four base sequences (CACC) were inserted into a pENTR/SD vector (Gateway system, Invitrogen). Then, 1 Tb and R1 were fused with each other using LTBR and R1F primers including BamHI restriction enzyme. Each gene (R1, R1R2, ltbR1 and ltbR1R2) was inserted into pENTR/SD and pDEST-42 vector (Gateway system, Invitrogen) pursuant to an instruction from each production company thereof. In order to express each recombinant protein, each gene inserted into the vector was transformed into *E. coli* BL21-competent cell by electroporation. Then, each *E. coli* BL21-competent cell was cultured in 1 L LB medium containing 100 μg/mL of ampicillin. Isopropyl-β-D-1-thiogalactopyranoside (IPTG) was added to a culturing liquid to reach a final concentration of 1 mM. Thus, protein expression was induced for 3 hours. The culturing liquid was subjected to sonication, and then centrifugation to obtain lysate including the recombinant protein. The expressed proteins were purified using HisPur Ni-NTA affinity chromatography (Thermo Scientific) according to an instruction from the manufacturer of the device. The amino acid sequence of the recombinant protein rP97 according to the present disclosure as produced finally was described in the SEQ ID NO.: 1. The base sequence encoding the amino acid sequence represented by the SEQ ID NO.: 1 is described in the SEQ ID NO.: 2. Further, the primer sequences as used are shown in SEQ ID NOS.: 3 to 12.

1.3 Producing of Vaccine

The inactivated and concentrated *Mycoplasma hyopneumoniae* was mixed aseptically with the excipient. Then, the mixture was diluted in a sterilized container as shown in Table 2. The diluted mixture was added to lysate including rP97, which, in turn, was mixed therewith for at least 30 minutes at 4° C. to produce the vaccine.

TABLE 2

| Vaccine | One-valent vaccine |
|---|---|
| *Mycoplasma hyopneumoniae* | $2.5 \times 10^8$ CCU/dose (Mhp HID3138, HID3117) |
| rP97 | Total lysate 300 μg/ml |
| Adjuvant | Montanide Gel: 20% Carbopol: 1 mg/ml |
| PBS | Make volume to 1 ml |
| Mixing time | At least 30 mins (4° C.) |

CCU = Colour-changing units (CCU)

1.4 Verification of Vaccine Effects Via Antibody Titer 1.4.1 Preparation of Experiment Group A 3-week-old swine free of *Mycoplasma hyopneumoniae* was used to measure the immunogenicity of the candidate vaccine. The presence or absence of *Mycoplasma hyopneumoniae* infection to all swine samples was checked at regular intervals using clinical data, presence or absence of pneumonia, other serological tests and ELISA kit (IDEXX Laboratories Inc., Westbrook, Me., USA). All swine were grouped into groups, each group having 5 pigs. 0.3 mg/ml of rP97 protein, Montanide Gel, Carbopol, produced in Example 1.2 was mixed to Mhp HID3138 and Mhp HID3117 inactivated by the method of Example 1.1 at the same mixing ratio as indicated at Table 2, thereby to produce present vaccines. The present vaccines were inoculated to each swine of the experiment group by 2 ml. Further, 1 ml of a commercial vaccine, Mycoflex® (Boehringer Ingelheim Animal Health, St. Joseph, Mo., USA) was inoculated to each swine of a comparative experiment group. Further, 2 ml of lysate including the rP97 recombinant protein alone as produced in Example 1.2 was inoculated to a lysate-treated comparative experiment group (rLysate). 2 ml of PBS alone was inoculated to a control. Thus, experiments were performed on total 5 groups. All groups were further inoculated 21 days after the initial inoculation. Serum samples were separated at 0, 21, 42, and 63 days after the initial vaccine inoculation and were stored at −20° C. until use in the experiment. Details about each experiment group are shown in Table 3 below.

TABLE 3

| Experiment group | Administered substance |
|---|---|
| G1 | Mhp HID3138 and rP97 recombinant protein-containing lysate |
| G2 | Mhp HID3117 and rP97 recombinant protein-containing lysate |
| G3 | rP97 recombinant protein-containing lysate |
| G4 | Saline alone |
| G5 | Commercial vaccine Mycoflex ® |

1.4.2. Antibody Titer Analysis Using ELISA

*Mycoplasma hyopneumoniae*-specific antibody titer was measured using IDEXX *M. hyo*. ELISA (IDEXX Laboratories Inc., Westbrook, Me., USA). The specific antibody titer for rP97 was checked using the expressed and purified P97 protein as an antigen. RP97 (0.5 μg/well) was coated on a 96-well Maxi-Sorp microtiter plate (NUNC, Thermo Scientific, Penfield, N.Y., USA) and stored at 4° C. for 16 hours. The plate was washed with PBS (PBST) containing 0.05% Tween 20, and then blocked with PBS (PBSM) containing 5% non-fat milk. After washing the plate three times with the PBST, 100 μl of serum (1:100 PBSM) was added to the plate. After washing the plate three times with PBST, horseradish peroxidase (HRP)-conjugated rabbit anti-porcine IgG (Sigma Aldrich, St. Louis, Mo., USA) was added to the plate and cultured. After washing the plate with PBST, reaction occurs with o-phenylenediamine (OPD) substrate (Sigma Aldrich, St. Louis, Mo., USA).

*Mycoplasma hyopneumoniae*-Specific Serologic Antibody Level Measurement

The results of *Mycoplasma hyopneumoniae*-specific serologic antibody levels as induced by various vaccine candidates were statistically analyzed using GraphPad Prism 5 software (GraphPad Software Inc., La Jolla, Calif., USA). Two-way ANOVA in combination with Bonferroni post-test was used to evaluate differences in serum antibody titers between the groups. Significant differences were expressed by $P<0.05$. Antibody level measurement results are illustrated in FIG. 1.

As illustrated in FIG. 1, the PBS treated control group exhibited a negative response throughout the inoculation. On the other hand, G1 and G2 groups exhibited positive responses from the 42 day after the inoculation until the end of the experiment. Further, the present vaccine-inoculated group exhibited a higher antibody level than the MFlex treated group G5, which is a commercial vaccine-inoculated group. The G2 group exhibited a similar level to that of the commercial vaccine group G5 at 63 days after the inoculation. The G1 and G2 groups induced the highest levels of the antibody at 42 and 63 days after the inoculation, which were statistically critical values when compared with the PBS-treated group.

Evaluation of rP97-Specific Immune Response

In order to evaluate the rP97-specific immune response, an indirect ELISA was performed using serum of vaccine-inoculated swine. The results are illustrated in FIG. 2.

As illustrated in FIG. 2, the rP97-specific antibody levels were continuously increased in the G1 and G2 and G3 experiment groups, showing the highest value at 42 days after the inoculation. In particular, at 42 and 63 days after the inoculation, G1, G2 and G3 groups showed significantly higher levels of antibody titer than Control ($P<0.001$), and there was no significant difference between the three vaccination groups G1, G2 and G3. At day 42 after the inoculation, the G1, G2 and G3 groups showed antibody titers of 19, 20 and 16 times higher than that of Control, respectively.

On the other hand, Control G4 and commercial vaccine group G5 showed no rP97-specific immune response. From these results, it may be confirmed that the antibody titer levels to the adhesion protein P97 are zero in the commercially available vaccines, whereas the vaccine produced in accordance with the present disclosure shows a high antibody titer to the rP97. This confirmation is consistent with previous reports that the commercial vaccines are not capable of generating the P97-specific antibody titers. Thus, the vaccine produced in accordance with the present disclosure may be found to be more effective via enabling the high antibody titer for rP97 than the conventional commercial vaccines.

1.5 Evaluation of Efficacy of Inactivated Vaccine in Swine

To evaluate the efficacy of the produced vaccine, we isolated the bacteria from the swine of the farm where mycoplasma is present. Mycoplasma specific PCR and ELISA antibody titers were examined to confirm that the mycoplasma was circulating in the farms. G1 group including Mhp HID3138 and rP97 among the vaccines produced in Example 1.4.1 was subjected to the vaccine treatment at 1 and 4 weeks. Clinical symptoms (presence or absence of cough, depression, nasal secretion) of the G1 group were observed for 3 weeks after the vaccination. After the 3 weeks, 5 subjects in each group were randomly selected and the gross lesion index of the lungs thereof was calculated. The evaluation method using the gross lesion index of the lung is to analyze the gross lesion of the lung regarding the respiratory disease. This was done by setting the total lung volume to 100 and dividing the 100 score based on a volume of each leaf and then analyzing the gross lesion presence or absence of each lung. The results are shown in Table 4.

TABLE 4

| Test group | Number of tested subjects | Clinical symptoms | | | Lung lesion index* |
| --- | --- | --- | --- | --- | --- |
| | | Cough | Depression | Nasal secretion | |
| Vaccine-inoculated group | 10 | 2/10 | 0/10 | 1/10 | 13.8 ± 4.9 |
| Control | 10 | 9/10 | 7/10 | 9/10 | 72.4 ± 8.3 |

*5 subjects in each group were randomly selected and the gross lesion index of the lungs thereof was measured As shown in Table 4, cough, depression, and nasal secretions were observed in the Control without vaccination, but such clinical symptoms were not observed in the vaccine-inoculated group. There was a significant difference between the control and vaccine-inoculated groups in terms of the gross lesion index of the lung. Thus, the vaccine produced in accordance with the present disclosure has been shown to reduce the respiratory symptoms and lung lesions when being inoculated to the swine on mycoplasma-present farms.

The above results suggest that recombinant protein rP97 according to the present disclosure may be useful for the vaccine against the Mycoplasma hyopneumoniae. Further, the vaccine including the recombinant protein may include a significant attachment factor P97, which is an important factor for early infection of the Mycoplasma hyopneumoniae, unlike the conventional vaccine free of the significant attachment factor P97. Thus, this may allow the clear formation of the antibody to allow checking whether the vaccine is inoculated. Further, this may prevent the transmission of the naturally infected bacteria and the colonization thereof on the respiratory cilium, which has been pointed out as a technical limitation of the conventional commercial vaccines. That is, the recombinant protein rP97 according to the present disclosure may effectively prevent the mycoplasma via inhibition of early onset of the Mycoplasma hyopneumoniae.

Example 2. Two-Valent Vaccine Including rP97m 2.1 Preparation of Mycoplasma Strain Mycoplasma hyopneumoniae (Mhp) and Mycoplasma hyorhinis (Mhr) strains were isolated from lungs showing swine Mycoplasma lung lesions and cultured for 3 days at 5% $CO^2$ and 37° C. using Friis medium. We confirmed via protein pattern analysis that strains Mhp HID3134, HID3140, HID3138, and Mhr HID3224 as isolated were different strains from standard strains of the Mycoplasma hyopneumoniae and Mycoplasma hyorhinis. These strains were expected to be highly pathogenic and high-titer strains inducing antibodies. The cultured inoculum was adjusted to pH 7.8 and then inactivated using an inactivating reagent such as Binary ethyleneimine (BEI) (U.S. Pat. No. 5,565,205). BEI was produced by adding L-bromoethylaminehydrobromide (BEA) (Sigma-Aldrich, St. Louis, Mo., USA) to the culture liquid. Then, neutralization was performed by adding sodium thiosulfate (Sigma-Aldrich, St. Louis, Mo., USA) as a neutralizing reagent thereto. A portion of the inactivated culture liquid was added to a new medium and cultured at 37° C., and was cultured for at least one week. Then, the inactivated state of the inactivated culture liquid was checked. Then, the inactivated culture liquid was concentrated by centrifugation.

2.2 Preparation of rP97m Protein

The recombinant protein rP97m was produced by fusing the P97 protein of the Mycoplasma hyopneumoniae and E. coli heat-labile enterotoxin subunit B (eltb). rP97 in Example 1 was obtained from Mhp without processing and then fused with LTB. However, rP97m was produced by separately producing R1 and R2 using the base sequence of R1 and R2, as core sites of P97, and fusing the R1 and R2 with LTB. More specifically, the recombination of the rP97m protein was performed using pET-30a (+) (Novagen, USA) expression system. The expression plasmids were inserted into E. coli BL21 codon-plus RIL competent cells (Novagen) using thermal shock, which, in turn, was cultured in 1 L of Luria-Bertani (LB) medium containing 50 µg/mL kanamycin. Protein expression was then induced for 3 hours with 1 mM isopropyl-β-D-1-thiogalactopyranoside (IPTG). The culturing liquid was subjected to sonication, and then centrifugation to obtain lysate including the recombinant protein. The Ni-NTA column was used to purify and concentrate the recombinant protein from the lysate. The amino acid sequence of the recombinant protein rP97m according to the present disclosure as produced is described in SEQ ID NO.: 13. The base sequence encoding the amino acid represented by SEQ ID NO.: 13 is described in SEQ ID NO.: 14.

Figure 3B:
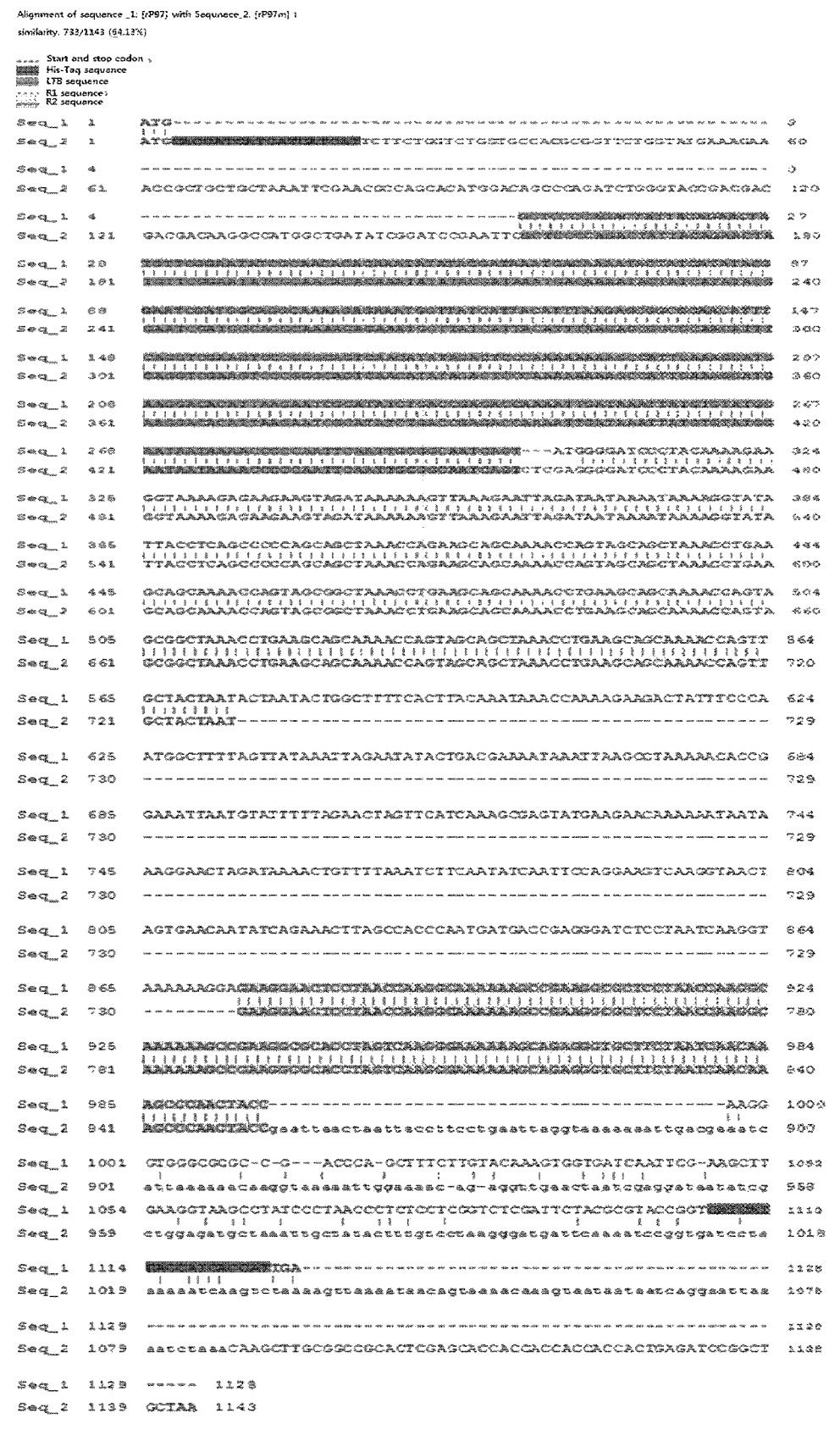

Further, the sequence structures and homology of rP97 and rP97m were compared with each other to confirm the similarity of the recombinant protein rP97 as produced in the Example 1.2 and the recombinant protein rP97m as produced in the Example 2.2. The results are illustrated in FIG. 3.

As illustrated in FIG. 3A, the rP97 and rP97m have mutually different structures. Especially, the rP97m results from individual synthesis of R1 and R2 to constitute only the essential sites. As illustrated in FIG. 3B, both the sequences showed 64.13% homology and showed very low homology.

2.3 Producing of Vaccine

The inactivated and concentrated *Mycoplasma hyopneumoniae* and *Mycoplasma hyorhinis* were aseptically mixed with the excipient. Then, the mixture was diluted in a sterilized container as shown in Table 5, and then was mixed for at least 24 hours.

TABLE 5

| Vaccine | Two-valent vaccine |
|---|---|
| *Mycoplasma hyopneumoniae* | $1.0 \times 10^9$ CCU/dose (Mhp HID3134, HID3140, or HID3138) |
| *Mycoplasma hyorhinis* | $1.0 \times 10^9$ CCU/dose (Mhr HID3224) |
| rP97m | Purified protein 100 μg/dose |
| Adjuvant | IMS1313: 50% |
| PBS | Make volume to 2 ml |
| Mixing time | At least 24 (4° C.) |

CCU = Colour-changing units (CCU)

2.4 Verification of Vaccine Effect 2.4.1 Preparation of Experiment Group

A 3-week-old swine free of *Mycoplasma hyopneumoniae* and *Mycoplasma hyorhinis* was used to measure the immunogenicity of the candidate vaccine. The presence or absence of *Mycoplasma hyopneumoniae* and *Mycoplasma hyorhinis* infection to all swine samples was checked at regular intervals using clinical symptoms, presence or absence of pneumonia, other serological tests and ELISA kit (IDEXX Laboratories Inc., Westbrook, Me., USA). All swine were grouped into groups, each group having 4 pigs. Mhp HID3134, Mhp HID3140, Mhp HID3138 and Mhr HID3224 which were inactivated by the method of Example 2.1 and rP97m were mixed with each other at a mixing ratio as in Table 5 to produce the present vaccine. Then, the present vaccines were administered to each swine of the experiment group by 2 ml once. Samples were collected 4 days before the inoculation, and in 1, 2, 4, and 5 weeks after the inoculation. Details about each experiment group are shown in Table 6 below. A comparative experiment group was set to a group treated with Respisure® (Zoetis, USA), a commercialized vaccine. After the inoculation of the vaccine, the blood was collected and the serum was separated and stored at −20° C.

TABLE 6

| Experiment group | Administered substance |
|---|---|
| GROUP 1(G1) | PBS alone |
| GROUP 2 (G2) | Commerical vaccine Respisure ® |
| GROUP 3 (G3) | Mhp HID3134 + Mhr HID3224 + rP97m |
| GROUP 4 (G4) | Mhp HID3140 + Mhr HID3224 + rP97m |
| GROUP 5 (G5) | Mhp HID3138 + Mhr HID3224 + rP97m |

2.4.2. Antibody Titer Analysis Using ELISA

*Mycoplasma hyopneumoniae*-specific antibody titer was measured using IDEXX *M. hyo*+. ELISA kit (IDEXX Laboratories Inc., Westbrook, Me., USA). The P97m specific antibody titer was measured by coating the purified protein rP97m as an antigen. The *Mycoplasma hyorhinis* specific antibody titer was measured by coating *Mycoplasma hyorhinis* whole bacterin as an antigen. Each antigen (rP97m: 0.2 μg/well, Mhr whole bacterin: 25 ng/well) was coated on a 96-well Maxi-Sorp microtiter plate (NUNC, Thermo Scientific, Penfield, N.Y., USA), which, in, turn, was stored for 16 hours at 4° C. and then for 2 hours at 37° C. The plate was washed three times with PBS-T supplemented with 0.05% Tween 20 and blocked with 1% BSA in PBS at 37° C. for 2 hours. After washing the plate three times with PBS-T, 100 μl of serum (1:100 dilution, 0.1% BSA in PBS) was added to the plate. Reaction occurred at 37° C. for 2 hours. After 3 times washing the plate with PBS-T, horseradish peroxidase (HRP)-conjugated goat anti-swine IgG (Abcam, UK) was added to the plate. Reaction occurred for 1 hour at 37° C. Then, the plate was washed four times with PBS-T. BioFX® TMB One Component HRP Microwell Substrate (SurModics®, USA) was added thereto and dark reaction occurred for 5 minutes at a room temperature and a reaction-stopper agent was added thereto to stop the reaction. Then, absorbance was measured at 450 nm and the results were confirmed.

*Mycoplasma hyopneumoniae*-Specific Serologic Antibody Level Measurement

Prior to the inoculation, all swine samples were serologically tested and then exhibited a negative response and then the experiment was executed. The results of *Mycoplasma hyopneumoniae*-specific serologic antibody levels as induced by the swine *Mycoplasma* two-valent vaccine candidates were statistically analyzed using GraphPad Prism 5 software (GraphPad Software Inc., La Jolla, Calif., USA). Two-way ANOVA in combination with Bonferroni post-test was used to evaluate differences in serum antibody titers between the groups. Significant differences were expressed by $P<0.05$. Antibody level measurement results are illustrated in FIG. 4.

As illustrated in FIG. 4, the PBS treated group G1 exhibited a negative response throughout the inoculation. On the other hand, it was confirmed that the G3, G4 and G5 groups exhibited positive responses from the two weeks after the inoculation until the end of the experiment such that the humoral immune response occurred. In particular, the antibody titer level was explosively increased from 2 weeks to 5 weeks after the vaccination, showing the higher antibody level than that of the commercial vaccine group G2 across the entire temporal region of the experiment. When compared with the PBS group G1, the G3, G4 and G5 groups exhibited the statistically significant values. These results suggest that the *mycoplasma* two-valent vaccine including the produced rP97m protein may induce the antibody in a greater performance than the commercially available vaccine induces. This result shows that rP97m protein may further promote the antibody formation reaction by the strain.

rP97-Specific Serological Antibody Level Measurement

In order to evaluate rP97m-specific immune responses induced by various vaccine candidates in an experiment using a swine *Mycoplasma* two-valent vaccine, an indirect ELISA was performed using serums from the vaccine-inoculated swine. The results are illustrated in FIG. 5.

As illustrated in FIG. 5, rP97m-specific antibody levels for vaccine-inoculated groups G3, G4, and G5 began to increase from day 14 after the inoculation. When compared with the PBS group G1, the rP97m-specific antibody levels for vaccine-inoculated groups G3, G4, and G5 have statistically significant values. In contrast, the rP97m-specific antibody was not detected in the commercial vaccine-inoculated group G2. These results show that the commercial vaccines do not include the P97 protein, which plays an important role for early defense against the swine *Mycoplasma*.

*Mycoplasma hyorhinis*-Specific Serological Antibody Level Measurement

The swine *Mycoplasma* two-valent vaccine includes the *Mycoplasma hyorhinis*. Therefore, the level of the antibody against the *Mycoplasma hyorhinis* was measured. The results are illustrated in FIG. 6. Similarly, all swine samples were serologically negative before the inoculation and then the experiment was executed.

As illustrated in FIG. 6, the PBS group G1 has a negative response throughout the inoculation. On the other hand, the group G3, G4, and G5, which were inoculated with the two-valent vaccine exhibited a positive response from the 4th week after the inoculation to the end of the experiment. The Group 4 treatment group had a statistically significant value when compared with the PBS group. Thus, it was confirmed that the Group 4 treatment group exhibited the humoral immune response. On the other hand, the *Mycoplasma hyorhinis* was not included in the commercial vaccine group G2 such that the *Mycoplasma hyorhinis*-specific antibody was not detected therein. This group G2 showed only the negative response until 5 weeks after the inoculation.

2.4.3 Identification of Cellular Immune Response by Inoculation with Two-Valent Vaccine To evaluate the cellular immunity of the swine *Mycoplasma* two-valent vaccine, PBMC (Peripheral Blood Mononuclear Cell) was isolated from the swine blood sample at two weeks after the inoculation, that is, at a timing when an antibody begins to be formed. The amount of IFN-γ as produced after stimulation with *Mycoplasma hyopneumoniae* was evaluated using a Swine INF-γ ELISA Kit from Novex company. The results are illustrated in FIG. 7.

As illustrated in FIG. 7, the commercial vaccine group showed only a low cellular immune response, whereas the G3, G4, and G5 groups vaccinated with the two-valent vaccine as produced in Example 2 have statistically significantly higher INF-γ production values than that of the commercial vaccine group G2. We also found that the two-valent vaccine as produced could induce a superior cellular immune response compared to the commercial vaccine group.

2.4.4 Identification of Side Effects by Two-Valent Vaccine Inoculation

To evaluate the side effects of the swine *Mycoplasma* two-valent vaccine, the body weights of the experimental groups were measured and compared to each other. In general, the side effects due to the vaccine inoculation may include symptoms such as inflammation, skin necrosis, seizures, etc. When the side effect is severe, this may cause death and impose damage to the farm. In addition, when the side effects after the vaccination appear, the feed intake amount by the swine will decrease rapidly and the growth rate of the swine will decrease. To evaluate whether or not the produced swine *Mycoplasma* two-valent vaccine causes adverse effects due to the vaccination thereof, the body weights of the control group G1, the commercial vaccine group G2 and the present vaccine-inoculated group G3, G4 and G5 were measured for five weeks after the inoculation. The results are illustrated in FIG. 8.

As illustrated in FIG. 8, there was no difference in the weight between the present vaccine-inoculated groups G3, G4, and G5, control group G1 and commercial vaccine group G2. Thus, we also found that the produced *mycoplasma* two-valent vaccine including rP97m could be used as a safe vaccine without side effects on swine.

The two-valent vaccine including the recombinant protein consisted of the amino acid sequence as represented by the SEQ ID NO.: 13 results in a high level of the *Mycoplasma hyopneumoniae* and *Mycoplasma hyorhinis*-specific humoral immune response, and a high level of the *Mycoplasma hyopneumoniae*-specific cellular immune response. Thus, the two-valent vaccine including the recombinant protein composed of the amino acid sequence as represented by the SEQ ID NO.: 13 may be more effective in terms of induction of the immune response than the commercially available vaccine.

The invention claimed is:

1. A recombinant protein for production of vaccine for prevention of swine *Mycoplasma hyopneumoniae* infection, the protein comprising an amino acid sequence represented by SEQ ID NO.: 1.

2. A polynucleotide encoding the recombinant protein of claim 1.

3. The polynucleotide of claim 2, wherein the polynucleotide is consisted of a base sequence represented by SEQ ID NO.: 2.

4. A vaccine composition for preventing *Mycoplasma hyopneumoniae* infection, the composition comprising the recombinant protein of claim 1.

5. The composition of claim 4, further comprising inactivated *Mycoplasma hyopneumoniae*.

6. The composition of claim 5, wherein the inactivated *Mycoplasma hyopneumoniae* is included at a concentration of $1.0 \times 10^6$ to $1.0 \times 10^{10}$ CCUs (colour-changing units)/ml.

7. A *Mycoplasma hyopneumoniae* infection-preventing vaccine adjuvant comprising the recombinant protein of claim 1.

8. A vaccine composition for preventing a disease caused by *Mycoplasma hyopneumoniae* infection, the composition comprising the recombinant protein of claim 1.

9. A method for producing a *Mycoplasma hyopneumoniae* infection-preventing vaccine adjuvant, the method comprising:
   1) producing a vector including a polynucleotide encoding a recombinant protein represented by SEQ ID NO.: 1;
   2) transforming a host using the vector; and
   3) expressing the recombinant protein in the transformed host.

10. A method for preventing swine *Mycoplasma hyopneumoniae* infection, the method comprising administering the vaccine composition of claim 8 to a swine.

11. A recombinant protein for production of a vaccine for prevention of swine *Mycoplasma hyopneumoniae* and *Mycoplasma hyorhinis* infection, the protein comprising an amino acid sequence represented by SEQ ID NO.: 13.

12. A polynucleotide encoding the recombinant protein of claim 11.

13. The polynucleotide of claim 12, wherein the polynucleotide is consisted of a base sequence represented by SEQ ID NO.: 14.

14. A swine *Mycoplasma hyopneumoniae* and *Mycoplasma hyorhinis* infection-preventing vaccine composition comprising the recombinant protein of claim 11.

15. The composition of claim 14, further comprising inactivated *Mycoplasma hyopneumoniae* and inactivated *Mycoplasma hyorhinis*.

16. The composition of claim 15, wherein the inactivated *Mycoplasma hyopneumoniae* or inactivated *Mycoplasma hyorhinis* is included at a concentration of $1.0 \times 10^6$ to $1.0 \times 10^{10}$ CCUs (colour-changing units)/ml.

17. A swine *Mycoplasma hyopneumoniae* and *Mycoplasma hyorhinis* infection-preventing vaccine adjuvant comprising the recombinant protein of claim 11.

18. A vaccine composition for preventing a disease caused by swine *Mycoplasma hyopneumoniae* and *Mycoplasma hyorhinis* infection, the composition comprising the recombinant protein of claim 11.

19. A method for producing a swine *Mycoplasma hyopneumoniae* and *Mycoplasma hyorhinis* infection-preventing vaccine adjuvant, the method comprising:
   1) producing a vector including a polynucleotide encoding a recombinant protein represented by SEQ ID NO.: 13;
   2) transforming a host using the vector; and
   3) expressing the recombinant protein in the transformed host.

20. A method for preventing swine *Mycoplasma hyopneumoniae* and *Mycoplasma hyorhinis* infection, the method comprising inoculating the vaccine composition of claim 14 to a swine.

\* \* \* \* \*

SEQUENCE LISTING

```
<160> NUMBER OF SEQ ID NOS: 14

<210> SEQ ID NO 1
<211> LENGTH: 274
<212> TYPE: PRT
<213> ORGANISM: artificial sequence
<220> FEATURE:
<223> OTHER INFORMATION: Mycoplasma hyopneumoniae rP97 protein sequence

<400> SEQUENCE: 1

Met Gly Ile Pro Thr Lys Glu Gly Lys Arg Glu Glu Val Asp Lys Lys
1               5                   10                  15

Val Lys Glu Leu Asp Asn Lys Ile Lys Gly Ile Leu Pro Gln Pro Pro
            20                  25                  30

Ala Ala Lys Pro Glu Ala Ala Lys Pro Val Ala Ala Lys Pro Glu Ala
        35                  40                  45

Ala Lys Pro Val Ala Ala Lys Pro Glu Ala Ala Lys Pro Glu Ala Ala
    50                  55                  60

Lys Pro Val Ala Ala Lys Pro Glu Ala Ala Lys Pro Val Ala Ala Lys
65                  70                  75                  80

Pro Glu Ala Ala Lys Pro Val Ala Thr Asn Thr Asn Thr Gly Phe Ser
                85                  90                  95

Leu Thr Asn Lys Pro Lys Glu Asp Tyr Phe Pro Met Ala Phe Ser Tyr
            100                 105                 110
```

Lys Leu Glu Tyr Thr Asp Glu Asn Lys Leu Ser Leu Lys Thr Pro Glu
            115                 120                 125

Ile Asn Val Phe Leu Glu Leu Val His Gln Ser Glu Tyr Glu Glu Gln
        130                 135                 140

Lys Ile Ile Lys Glu Leu Asp Lys Thr Val Leu Asn Leu Gln Tyr Gln
145                 150                 155                 160

Phe Gln Glu Val Lys Val Thr Ser Glu Gln Tyr Gln Lys Leu Ser His
                165                 170                 175

Pro Met Met Thr Glu Gly Ser Pro Asn Gln Gly Lys Lys Gly Glu Gly
            180                 185                 190

Thr Pro Asn Gln Gly Lys Lys Ala Glu Gly Ala Pro Asn Gln Gly Lys
        195                 200                 205

Lys Ala Glu Gly Ala Pro Ser Gln Gly Lys Lys Ala Glu Gly Ala Ser
    210                 215                 220

Asn Gln Gln Ser Pro Thr Thr Lys Gly Gly Arg Ala Asp Pro Ala Phe
225                 230                 235                 240

Leu Tyr Lys Val Val Ile Asn Ser Lys Leu Glu Gly Lys Pro Ile Pro
                245                 250                 255

Asn Pro Leu Leu Gly Leu Asp Ser Thr Arg Thr Gly His His His His
            260                 265                 270

His His

<210> SEQ ID NO 2
<211> LENGTH: 825
<212> TYPE: DNA
<213> ORGANISM: artificial sequence
<220> FEATURE:
<223> OTHER INFORMATION: Mycoplasma hyopneumoniae rP97 DNA sequence

<400> SEQUENCE: 2

```
atggggatcc ctacaaaaga aggtaaaaga gaagaagtag ataaaaaagt taagaattta      60
gataataaaa taaaaggtat attacctcag cccccagcag ctaaaccaga agcagcaaaa     120
ccagtagcag ctaaacctga agcagcaaaa ccagtagcgg ctaaacctga agcagcaaaa     180
cctgaagcag caaaaccagt agcggctaaa cctgaagcag caaaaccagt agcagctaaa     240
cctgaagcag caaaaccagt tgctactaat actaatactg gcttttcact tacaaataaa     300
ccaaaagaag actatttccc aatggctttt agttataaat tagaatatac tgacgaaaat     360
aaattaagcc taaaaacacc ggaaattaat gtattttag aactagttca tcaaagcgag     420
tatgaagaac aaaaaataat aaaggaacta gataaaactg tttaaatct tcaatatcaa     480 ttccaggaag tcaaggtaac tagtgaacaa tatcagaaac ttagccaccc aatgatgacc     540
gagggatctc ctaatcaagg taaaaaagga gaaggaactc ctaaccaagg caaaaaagcc     600
gaaggcgctc ctaaccaagg caaaaaagcc gaaggcgcac ctagtcaagg gaaaaaagca     660
gagggtgctt ctaatcaaca agcccaact accaagggtg gcgcgccga cccagctttc     720 ttgtacaaag tggtgatcaa ttcgaagctt gaaggtaagc ctatccctaa ccctctcctc     780
ggtctcgatt ctacgcgtac cggtcatcat caccatcacc attga                    825
```

<210> SEQ ID NO 3
<211> LENGTH: 25
<212> TYPE: DNA
<213> ORGANISM: artificial sequence
<220> FEATURE:
<223> OTHER INFORMATION: LTB Forward primer

<400> SEQUENCE: 3

```
caccatggct ccccagacta ttaca                                    25

<210> SEQ ID NO 4
<211> LENGTH: 21
<212> TYPE: DNA
<213> ORGANISM: artificial sequence
<220> FEATURE:
<223> OTHER INFORMATION: LTB Reverse primer

<400> SEQUENCE: 4
ctggatcccc atactgattg c                                        21

<210> SEQ ID NO 5
<211> LENGTH: 26
<212> TYPE: DNA
<213> ORGANISM: artificial sequence
<220> FEATURE:
<223> OTHER INFORMATION: R1 Forward primer

<400> SEQUENCE: 5
caccatgggg atccctacaa aagaag                                   26

<210> SEQ ID NO 6
<211> LENGTH: 22
<212> TYPE: DNA
<213> ORGANISM: artificial sequence
<220> FEATURE:
<223> OTHER INFORMATION: R1  Reverse primer

<400> SEQUENCE: 6
gccaagctta gtagcaactg gt                                       22

<210> SEQ ID NO 7
<211> LENGTH: 26
<212> TYPE: DNA
<213> ORGANISM: artificial sequence
<220> FEATURE:
<223> OTHER INFORMATION: R1 Forward primer

<400> SEQUENCE: 7
caccatgggg atccctacaa aagaag                                   26

<210> SEQ ID NO 8
<211> LENGTH: 18
<212> TYPE: DNA
<213> ORGANISM: artificial sequence
<220> FEATURE:
<223> OTHER INFORMATION: 2Rs Reverse primer

<400> SEQUENCE: 8
ggtagttggg ctttgttg                                            18

<210> SEQ ID NO 9
<211> LENGTH: 25
<212> TYPE: DNA
<213> ORGANISM: artificial sequence
<220> FEATURE:
<223> OTHER INFORMATION: LTB Forward primer

<400> SEQUENCE: 9
caccatggct ccccagacta ttaca                                    25

<210> SEQ ID NO 10
<211> LENGTH: 22
<212> TYPE: DNA
```

```
<213> ORGANISM: artificial sequence
<220> FEATURE:
<223> OTHER INFORMATION: R1 Reverse primer

<400> SEQUENCE: 10
gccaagctta gtagcaactg gt                                                  22

<210> SEQ ID NO 11
<211> LENGTH: 25
<212> TYPE: DNA
<213> ORGANISM: artificial sequence
<220> FEATURE:
<223> OTHER INFORMATION: LTB Forward primer

<400> SEQUENCE: 11
caccatggct ccccagacta ttaca                                               25

<210> SEQ ID NO 12
<211> LENGTH: 18
<212> TYPE: DNA
<213> ORGANISM: artificial sequence
<220> FEATURE:
<223> OTHER INFORMATION: 2RsR

<400> SEQUENCE: 12
ggtagttggg ctttgttg                                                       18

<210> SEQ ID NO 13
<211> LENGTH: 380
<212> TYPE: PRT
<213> ORGANISM: artificial sequence
<220> FEATURE:
<223> OTHER INFORMATION: Mycoplasma hyopneumoniae rP97m protein sequence

<400> SEQUENCE: 13
```

Met His His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser Glu Phe Ala Pro Gln Thr Ile Thr Glu Leu Cys Ser Glu Tyr
    50                  55                  60

Arg Asn Thr Gln Ile Tyr Thr Ile Asn Asp Lys Ile Leu Ser Tyr Thr
65                  70                  75                  80

Glu Ser Met Ala Gly Lys Arg Glu Met Val Ile Ile Thr Phe Lys Ser
                85                  90                  95

Gly Ala Thr Phe Gln Val Glu Val Pro Gly Ser Gln His Ile Asp Ser
            100                 105                 110

Gln Lys Lys Ala Ile Glu Arg Met Lys Asp Thr Leu Arg Ile Ala Tyr
        115                 120                 125

Leu Thr Glu Thr Lys Ile Asp Lys Leu Cys Val Trp Asn Asn Lys Thr
    130                 135                 140

Pro Asn Ser Ile Ala Ala Ile Ser Leu Glu Gly Ile Pro Thr Lys Glu
145                 150                 155                 160

Gly Lys Arg Glu Glu Val Asp Lys Lys Val Glu Leu Asp Asn Lys
                165                 170                 175

Ile Lys Gly Ile Leu Pro Gln Pro Pro Ala Ala Lys Pro Glu Ala Ala
            180                 185                 190

Lys Pro Val Ala Ala Lys Pro Glu Ala Ala Lys Pro Val Ala Ala Lys

```
            195                 200                 205
Pro Glu Ala Ala Lys Pro Glu Ala Ala Lys Pro Val Ala Ala Lys Pro
        210                 215                 220

Glu Ala Ala Lys Pro Val Ala Ala Lys Pro Glu Ala Ala Lys Pro Val
225                 230                 235                 240

Ala Thr Asn Glu Gly Thr Pro Asn Gln Gly Lys Lys Ala Glu Gly Ala
                245                 250                 255

Pro Asn Gln Gly Lys Lys Ala Glu Gly Ala Pro Ser Gln Gly Lys Lys
            260                 265                 270

Ala Glu Gly Ala Ser Asn Gln Gln Ser Pro Thr Thr Glu Leu Thr Asn
        275                 280                 285

Tyr Leu Pro Glu Leu Gly Lys Lys Ile Asp Glu Ile Ile Lys Lys Gln
290                 295                 300

Gly Lys Asn Trp Lys Thr Glu Val Glu Leu Ile Glu Asp Asn Ile Ala
305                 310                 315                 320

Gly Asp Ala Lys Leu Leu Tyr Phe Val Leu Arg Asp Asp Ser Lys Ser
                325                 330                 335

Gly Asp Pro Lys Lys Ser Ser Leu Lys Val Lys Ile Thr Val Lys Gln
            340                 345                 350

Ser Asn Asn Asn Gln Glu Leu Lys Ser Lys Gln Ala Cys Gly Arg Thr
        355                 360                 365

Arg Ala Pro Pro Pro Pro Leu Arg Ser Gly Cys
        370                 375                 380

<210> SEQ ID NO 14
<211> LENGTH: 1143
<212> TYPE: DNA
<213> ORGANISM: artificial sequence
<220> FEATURE:
<223> OTHER INFORMATION: Mycoplasma hyopneumoniae rP97m DNA sequence

<400> SEQUENCE: 14
atgcaccatc atcatcatca ttcttctggt ctggtgccac gcggttctgg tatgaaagaa      60
accgctgctg ctaaattcga cgccagcac atggacagcc cagatctggg taccgacgac     120
gacgacaagg ccatggctga tatcggatcc gaattcgctc cccagactat tacagaacta     180
tgttcggaat atcgcaacac acaaatatat acgataaatg acaaaatact atcatatacg     240
gaatcgatgg caggcaaaag agaaatggtt atcattacat ttaagagcgg cgcaacattt     300
caggtcgaag tcccgggcag tcaacatata gactcccaaa aaaaagccat gaaaggatg     360 aaggacacat taagaatcgc atatctgacc gagaccaaaa ttgataaatt atgtgtatgg     420
aataataaaa cccccaattc aattgcggca atcagtctcg agggatccc tacaaaagaa     480 ggtaaaagag aagaagtaga taaaaaagtt aagaattag ataataaaat aaaaggtata     540
ttacctcagc ccccagcagc taaaccagaa gcagcaaaac cagtagcagc taaacctgaa     600
gcagcaaaac cagtagcggc taaacctgaa gcagcaaaac ctgaagcagc aaaaccagta     660
gcggctaaac ctgaagcagc aaaaccagta gcagctaaac ctgaagcagc aaaaccagtt     720
gctactaatg aaggaactcc taccaaggc aaaaaagccg aaggcgctcc taaccaaggc     780
aaaaaagccg aaggcgcacc tagtcaaggg aaaaaagcag agggtgcttc taatcaacaa     840
agcccaacta ccgaattaac taattacctt cctgaattag gtaaaaaaat tgacgaaatc     900
attaaaaaac aaggtaaaaa ttggaaaaca gaggttgaac taatcgagga taatatcgct     960
ggagatgcta aattgctata ctttgtccta agggatgatt caaaatccgg tgatcctaaa    1020
```

-continued

```
aaatcaagtc taaaagttaa aataacagta aaacaaagta ataataatca ggaattaaaa    1080
tctaaacaag cttgcggccg cactcgagca ccaccaccac caccactgag atccggctgc    1140
taa                                                                  1143
```